(12) United States Patent
Malin (10) Patent No.: US 8,092,743 B2
(45) Date of Patent: Jan. 10, 2012

(54) DEVICE FOR HANDLING LABORATORY SAMPLES

(75) Inventor: Cosmas G. Malin, Mauren (LI)

(73) Assignee: Liconic AG, Mauren (LI)

( * ) Notice: Subject to any disclaimer, the term of this patent is extended or adjusted under 35 U.S.C. 154(b) by 256 days.

(21) Appl. No.: 12/349,754

(22) Filed: Jan. 7, 2009

(65) Prior Publication Data
US 2009/0175763 A1 Jul. 9, 2009

(30) Foreign Application Priority Data
Jan. 8, 2008 (CH) .................................. 0021/08

(51) Int. Cl.
*G01N 35/10* (2006.01)
(52) U.S. Cl. ................ 422/65; 435/286.2; 436/47

(58) Field of Classification Search ............... 422/65; 435/286.2; 436/47
See application file for complete search history.

(56) References Cited

U.S. PATENT DOCUMENTS

| | | | | |
|---|---|---|---|---|
| 5,398,556 A | * | 3/1995 | Lang ........................... | 73/863.11 |
| 2002/0090320 A1 | * | 7/2002 | Burow et al. .................. | 422/64 |
| 2007/0254277 A1 | * | 11/2007 | Scrabeck et al. .................. | 435/4 |
| 2008/0253870 A1 | * | 10/2008 | Ford ......................... | 414/225.01 |

* cited by examiner

*Primary Examiner* — In Suk Bullock
*Assistant Examiner* — Timothy G Kingan
(74) *Attorney, Agent, or Firm* — Greenblum & Bernstein, P.L.C.

(57) ABSTRACT

A device for handling of laboratory samples includes at least one gripper movable from above over a sample. The gripper includes multiple fingers arranged around an axis, an elastic finger mount, and an actuator mechanism structured and arranged to move the fingers to selectively grip or release the sample. The multiple fingers are elastically held by the elastic finger mount in a radially displaceable manner.

21 Claims, 8 Drawing Sheets

DEVICE FOR HANDLING LABORATORY SAMPLES

CROSS REFERENCE TO RELATED APPLICATIONS

This application claims priority claims priority under 35 U.S.C. §119 of Swiss patent application CH 0021/08, filed Jan. 8, 2008, the disclosure of which is incorporated herein by reference in its entirety.

BACKGROUND OF THE INVENTION

1. Field of the Invention

The invention relates to a device for handling laboratory samples with a gripper or an ejection device.

2. Discussion of Background Information

For the handling of laboratory samples, particularly of containers for liquids, such as test tubes and small bottles, automated devices are often used in laboratories. These comprise, for example, a gripper, which can be lowered onto a sample and has multiple fingers arranged around an axis. The fingers are pushed sideways against the laboratory sample in order to gather it. Thereafter, the gripper can transport the sample to a desired place and put it down or carry out other manipulations with the sample.

In order to move the fingers of the gripper, an actuator mechanism is used. For example a rotatable plate is provided, in which a spiral groove is arranged, wherein the fingers are guided. By rotating the plate, the fingers can be moved radially towards the axis.

SUMMARY OF THE INVENTION

According to an aspect of the invention, embodiments of the invention provide a device of the type generally discussed above with a mechanically simple construction.

According to embodiments of the invention, a device for handling of laboratory samples includes at least one gripper movable from above over a sample. The gripper includes multiple fingers arranged around an axis, and an elastic finger mount. The multiple fingers are elastically held by said elastic finger mount in a radially displaceable manner. An actuator mechanism is provided for moving the fingers in order to grip or to dump the sample.

This allows carrying out a spreading or a contraction movement in a simple way, as the actuator mechanism moves the fingers against the spring force.

In embodiments, the actuator mechanism includes an actuation member which is arranged concentrically to the axis and which can be moved along the axis by an actuation drive. It is connected to the fingers in such a way that its axial movement is converted into a radial movement. For this, each finger can comprise, for example, a camming face that contacts the actuation member and forms a sort of wedge which is radially pressed or pulled by the movement of the actuation member.

Leaf springs are particularly adequate for holding the fingers because they allow to radially, elastically hold the fingers but to lead them tangentially and axially in a precise way.

The term "leaf spring" in the present text is to be understood as a spring formed by at least one longitudinal plate of elastic material, which plate can be bent about an axis parallel to the plate's major surfaces and perpendicular to the plate's longitudinal axes.

In embodiments, each finger is attached to at least two parallel leaf springs, which are arranged spaced-apart from each other. These form a sort of parallelogram guidance which avoids a tilt of the fingers relatively to the axis, such that it always abuts in planar manner against the laboratory sample.

In another aspect of the invention, a device of the initially mentioned type is provided with a compact construction.

According to embodiments, a device for handling samples includes at least one gripper movable from above over a sample and comprising multiple fingers arranged around an axis. The fingers are laterally pushable against the sample in order to grip the sample. A table on which the samples are graspable by the gripper is included. The table is movable in a first horizontal direction X and the gripper is movable in a second horizontal direction Y.

This device makes it is possible to access each storage location of a two-dimensional storage matrix on the table. By locally separating the displacements in directions X and Y (the first one is implemented at the table, the latter one at the gripper), a compact and stable construction can be realized, which would not be possible with a conventional X-Y-table.

In a further aspect of the invention, a device addresses the problem that, while taking or putting down samples, the sample itself or vicinal samples are not correctly put down and/or taken up accidentally, e.g., because they stick to the fingers of the gripper.

Accordingly, a device for handling laboratory samples includes at least one gripper movable from above over a sample and comprising multiple fingers arranged around an axis. The fingers are laterally pushable against the sample in order to grip the sample. An actuator mechanism for moving the fingers in order to grip and dump the sample is provided. The gripper includes at least one spring member which is compressible parallel to the axis The spring member is adapted to axially push, while taking on a laboratory sample, against the laboratory sample and/or against laboratory samples adjacent to the laboratory samples to be taken on.

In a further aspect of the invention, a device of the initially described type is provided that allows transferring samples from a first sample support to a second sample support.

Accordingly, a device for handling laboratory samples includes a stationary base, a table movable in a first horizontal direction X with respect to the base, and at least one upper sample holder and at least one lower sample holder, which are arranged on the table and each of which has an arrangement of storage positions for an accommodation of samples. The upper sample holder is arranged higher than the lower sample holder. A lift is arranged on the base with a vertically movable wagon, and an ejection device with a plunger, movable in a second horizontal direction Y, is arranged on the wagon. A sample intermediate storage is arranged below and spaced from the plunger, is arranged in a vertical direction Z between the upper and the lower sample holders, and is coupled with the ejection device for being commonly moved with the ejection device in said direction Y. A sample is pushable with the plunger, from above, out of a first storage position of the upper storage holder, into the sample intermediate storage as well as from the sample intermediate storage into a second storage position of the lower storage holder.

These components are formed in such a way that a sample can be pushed from above from a storage position of the upper sample support into the intermediate sample storage, by the plunger, as well as from the intermediate sample storage into another storage position of the lower sample support.

BRIEF DESCRIPTION OF THE DRAWINGS

The invention will be better understood and objects other than those set forth above will become apparent when consideration is given to the following detailed description thereof. Such description makes reference to the annexed drawings, which show.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
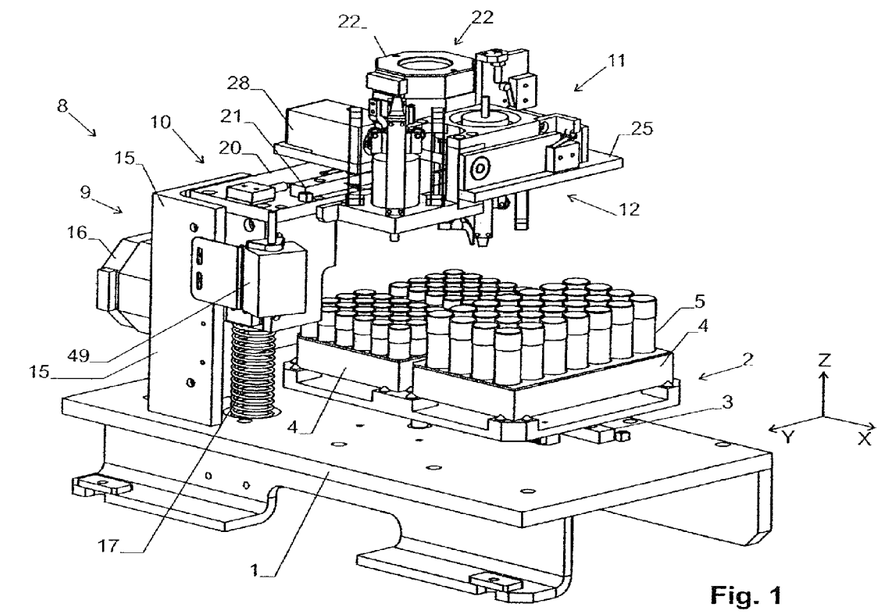
FIG. 1 shows a view of an embodiment of a device for handling laboratory samples.
Figure 2:
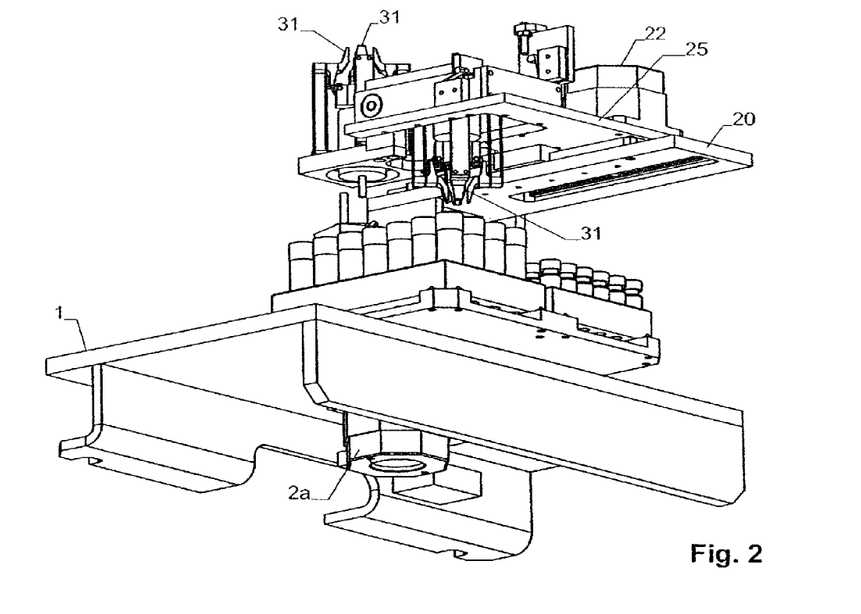
FIG. 2 shows a view of the embodiment of FIG. 1 from another direction, slightly from below.

The device for handling laboratory samples shown in FIGS. 1 and 2 comprises a stationary base 1, which carries a table 2. The table 2 is slidable along a rail 3 in a horizontal direction X, by an actuator 2a (see FIG. 2), and it carries, in the present embodiment, two sample holders 4. The sample holders 4 are preferably standardized components, as they are used in the laboratory domain for taking on a plurality of laboratory samples 5. The laboratory samples 5 stand in cavities of the sample holders 4, and each sample holder 4 has a two-dimensional matrix of such cavities.

A manipulation device 8 is arranged on the base 1, includes a lift 9, movable in vertical direction Z, and positioned on the base 1, which carries a wagon 10. The wagon 10 carries a holder 11 that is movable in horizontal direction Y, perpendicular to X and Z. A gripper 12 is arranged in such a way, that it swings around the direction X. In the following, these individual parts are described in detail.

The lift 9 comprises a tower 15, which is fixedly connected to the base 1. A rail (not shown) is attached to the tower 15, in which the wagon 10 moves along the direction Z. A lift actuator 16 is provided at the tower 15 in order to actuate the wagon 10, which operates a bevel wheel that drives the wagon 10 over a toothed bar. A compression spring takes on a part of the load of wagon 10 and reduces, in this a way, the load on the lift actuator 16.

The wagon 10 comprises a horizontal arm 20, which is provided with a guide 21, along which the holder 11 is slidable along direction Y. A horizontal actuator 22 is provided for the actuation of the holder 11.

Figure 6:
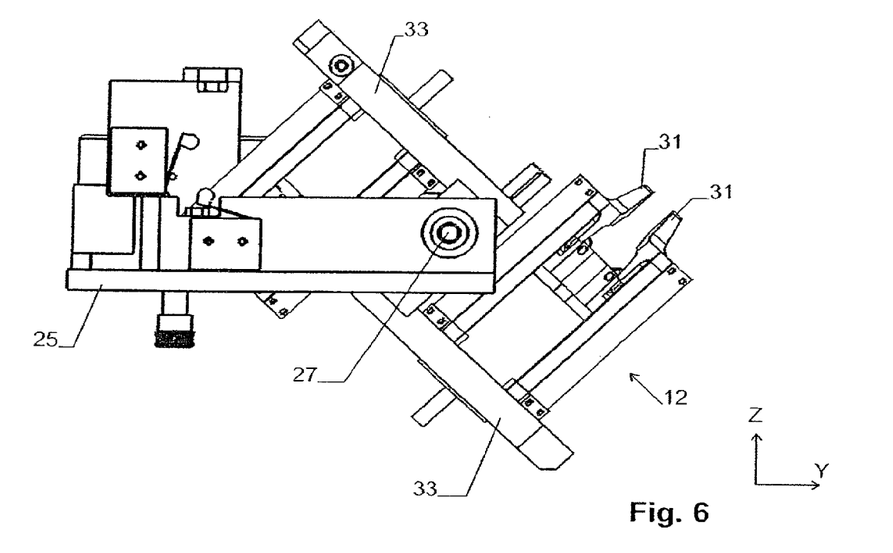
FIG. 6 shows a side view of the gripper and of a part of its support in inclined position.
Figure 7:
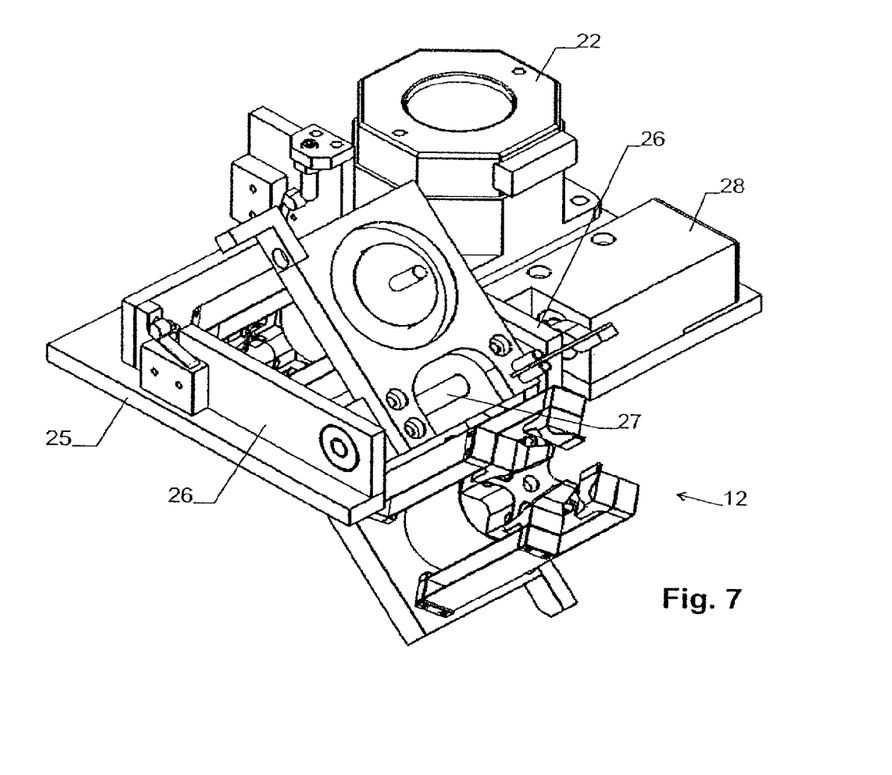
FIG. 7 shows a further view of the arrangement of FIG. 6.

The holder 11, which best can be seen in FIG. 6 and FIG. 7, has a horizontal plate 25, on which two storage elements 26 are arranged. These carry a pivot axle 27 defining a pivot axis, which extends in direction X and which can be swung by a swinging actuator 28 arranged on the holder 11. The actual gripper 12 is fixedly attached to the pivot axle 27 and can be swung around 180 degrees.

Figure 3:
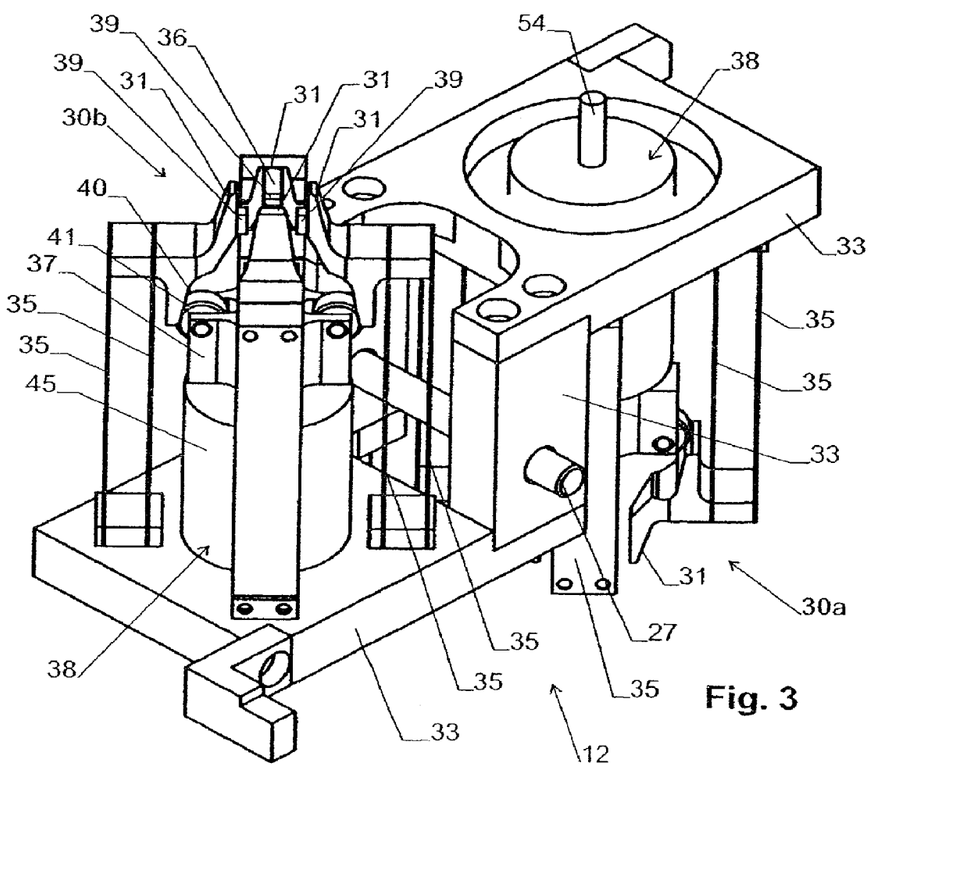
FIG. 3 shows a view of the gripper of the device from FIG. 1.
Figure 4:
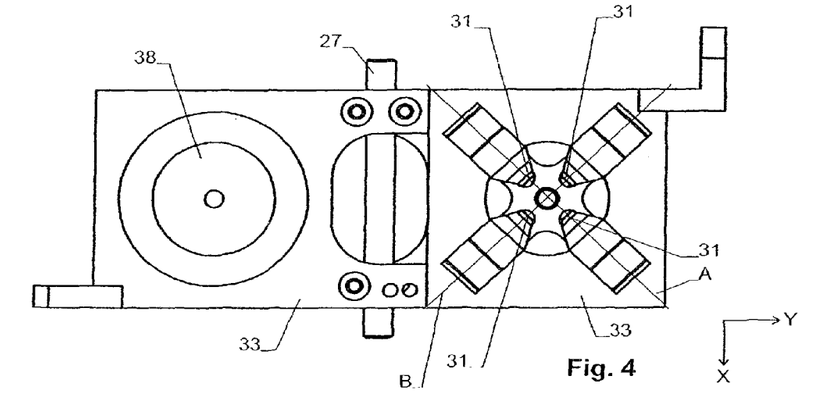
FIG. 4 shows a top view on the gripper of FIG. 3.
Figure 5:
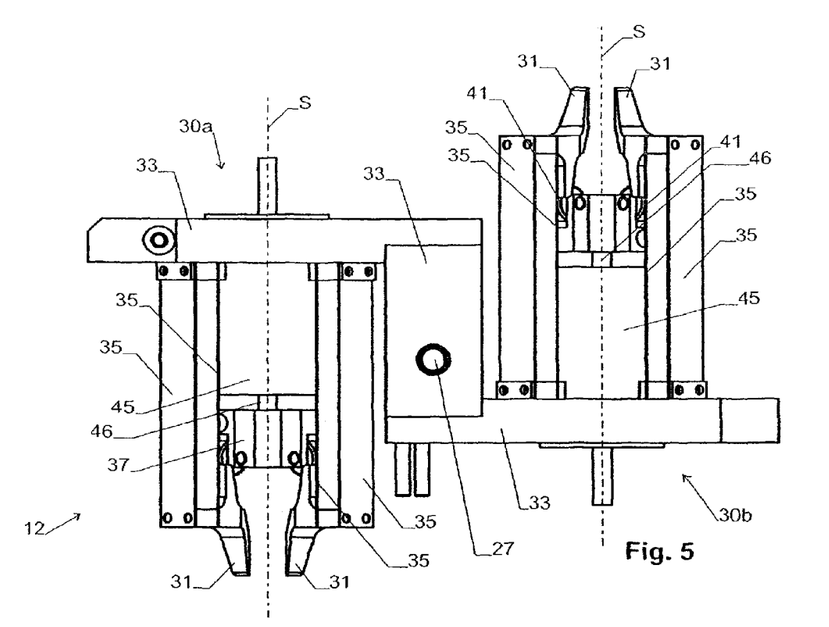
FIG. 5 shows a side view of the gripper of FIG. 3.

The gripper 12, whose construction can be best seen in FIG. 3 to 5, is equipped in the present example, with two gripping hands 30a, 30b, each equipped with four fingers 31 for gripping of the laboratory samples. These gripping hands have different gripping diameters, meaning that they are outfitted to manipulate laboratory samples with different diameters. The gripping hands 30a, 30b are mounted to a common carrier 33. Depending on which samples have to be manipulated, one or the other gripping hand 30a, 30b, respectively, can be brought into a working position, in which its fingers 31 are directed downwards and can be brought into contact the laboratory samples, by pivoting the gripper 12, i.e. the carrier 33, around the axle 27. Also, three or more gripper hands can be provided, one of which at a time can be brought into a working position while the rest of the gripper hands are located in idle positions. FIGS. 6 and 7 show the gripper 12 during the pivotal movement, while FIGS. 4 and 5 show the gripper in one of its two working positions, in which the gripping hand 30a is located in working position while the gripping hand 30b is located in idle position. In order to switch between both gripping hands 30a, 30b, the gripper 12 has to be pivoted by 180° around the pivot axle 27.

Figure 16:
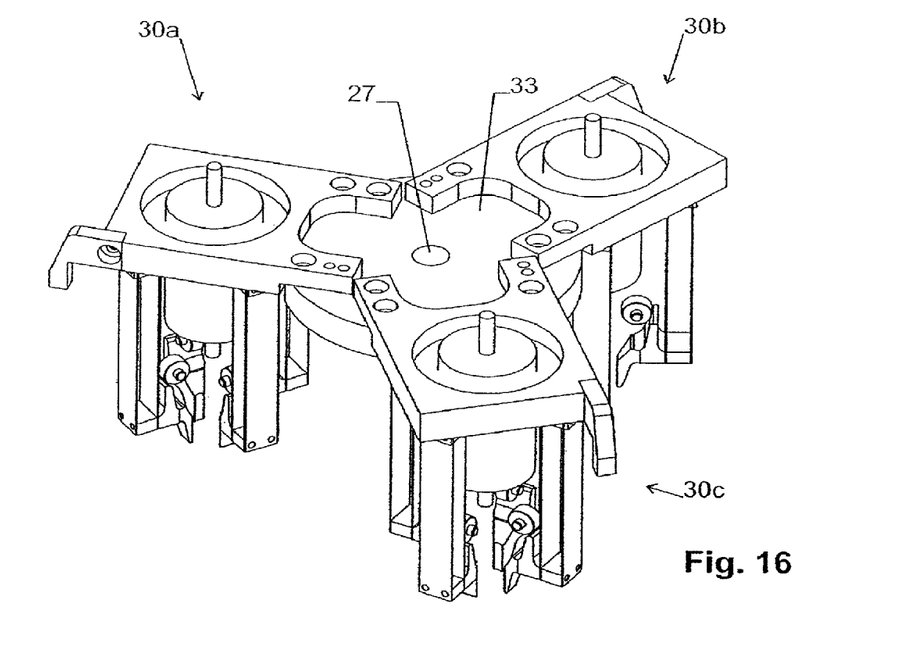
FIG. 16 shows an embodiment with three gripping hands.

As seen in FIG. 16, more than two gripping hands can be provided on the common carrier 33 as well, for example three gripping hands 30a, 30b, 30c, which are arranged mutually in parallel and rotationally symmetrically around a vertical pivot axis 27.

Each gripping hand 30a, 30b comprises, as mentioned, four fingers 21, but they may also have three or more than four fingers. For laboratory samples which have only to be gripped from two sides, only two fingers may suffice. However, the usage of four fingers is advantageous because, when cylindrical laboratory samples are used in a two-dimensional matrix, four void spaces are formed around each sample, which offer space for inserting the fingers. As seen in FIG. 4, the fingers are therefore arranged two at the time in planes A and B, respectively, which planes extend at +45 respectively −45 degrees in respect to the directions X and Y.

The fingers 31 of each gripper 30a, 30b are arranged symmetrically around a vertical axis S, which is shown in FIG. 5. They are elastically displaceable in radial direction in respect to the axis and can be moved by an actuator mechanism. In the following, this will be described in more detail.

As shown in FIG. 3, a member 39 made of foamed material (or of another material which is easier deformable than the finger itself) is attached to each finger 31 on the side facing the axis S. These members 39 make it easy to grip substantially flat objects like for example glass bottles.

As particularly seen in FIGs. 3 and 5, the gripper 12 comprises a carrier 33, which is fixedly connected to the axle 27 and which carries each of the gripping hands 30a, 30b. Each finger 31 is elastically attached to the carrier 33, preferably by two parallel leaf springs 35, which are arranged in spaced-apart manner, i.e., at a distance, from each other. The leaf springs 35 form an elastic finger mount for elastically holding the fingers 31 in a radially displaceable manner.

As mentioned at the beginning, the usage of two (or more) parallel leaf springs at a distance from each other guarantees that, during the finger movement described in more detail below, the fingers are not tilted but undergo only a translation without rotation, such that their inner faces 36 always remain vertical and can lie in a planar manner onto the vertical outer faces of the laboratory objects. If this advantage is not required, it is possible to use only a single leaf spring.

Each leaf spring extends, in an unstressed state, with its longitudinal direction substantially parallel to axis S and lies in a plane that is tangential to axis S. Each leaf spring 35 is connected at a first end to the carrier 33 and at the second end, opposite to the first end, to the respective finger 31. Hence, the second finger-sided end of each leaf spring 35 is radially elastically displaceable, while it substantially cannot be displaced in tangential direction.

The actuator mechanism for the fingers 31 comprises an actuation member 37, which is arranged concentrically to axis S and can be moved by an actuation drive 38 along the axis S. An anchor 54 of the actuation member extends through the actuation drive 38. The fingers 31 can be moved in radial direction (i.e. perpendicular to axis S) by an appropriate force redirection of the axial movement of the actuation member 37.

In the embodiment shown in FIGS. 3-5, each finger 31 comprises a camming face 40 (see FIG. 3), which is inclined to the axis and contacts one of four rolls 41 of the actuation member. The camming faces 40 are arranged on the side of the fingers facing the axis S and extend in such a way that, by moving the actuation member 37 towards the fingers 31, the fingers are pressed apart against the force of the leaf springs 35. The rolls 41 (the rotation axes of which are tangential to axis S) move along the camming faces 40 with little friction. At least one roll 41 is provided per camming face 40.

The actuator drive 38 has to be able to create a linear movement of the actuation member 37 along the axis S. In an exemplary embodiment, the actuator drive 38 comprises an electromagnet 45, which, when being flown through by a current, is able to move a piston 46 (FIG. 5) attached to the actuation member 37 in a direction along the axis S. In this manner, the fingers 31 are moved against the force of the leaf springs 35 from their inner position, in which they can grip the laboratory samples, into their outer position, in which they release the laboratory samples. If the current through the electromagnet is discontinued, the fingers 31 fall back into their inner position and thereby also press the piston 36 back into its initial position. In this manner it is achieved that, in case of a power cut, a gripped laboratory sample will not be dropped.

The actuator drive 38 is fixedly connected to the carrier 33. The actuator drive 38 and the actuation member 37 are on the inside of the leaf springs 35 (i.e. between the leaf springs and the axis S) such that the available space is best used.

The operation of the described device is as follows:

In order to take up a sample, the table 2 with the sample holders 4 is first displaced in such a way along direction X that the desired sample takes on the correct position in direction X. At the same time, the holder 11 is displaced in such a way in direction Y that the axis S of the desired gripping hand 30a, 30b (which was brought into its working position in advance) comes to lie coaxially to the desired sample in direction Y. Then, the wagon 10 is lowered in direction Z and at the same time the actuation member 37 is actuated, whereby the fingers 31 are brought into their outer position. The gripper 12 is lowered so far over the sample that the fingers 31 are located laterally to the sample and at the same height as the sample. Then, the actuation member 37 is released, such that the fingers 31 fall back into their inner position and thereby grip the sample. Wagon 10 can now be lifted so that the sample can be taken out the sample holder 4. The sample can then be driven to a desired position in Y and Z direction or, if needed, inclined by a rotation around axle 27. In order to put the sample down, the respective inverse motion sequence is carried out.

In order to identify samples, in the present embodiment a mark reader, arranged fixedly at the tower 15 and capable of automatically reading an identification mark located on the side of the sample, is arranged on the device. This can be, e.g., a bar code reader. In order to identify a sample, the sample can be brought to the mark reader by moving the wagon 10 in direction Y and be scanned there.

If single samples have to be taken out of sample holders in which the samples are situated close together, the situation can arise that, while taking on a sample, one or more neighbouring samples are accidentally moved, even lifted a bit, if the fingers 31 are not precisely positioned and inadvertently touch the neighboring samples. This problem is resolved by the solution according to FIG. 8.

Figure 8:
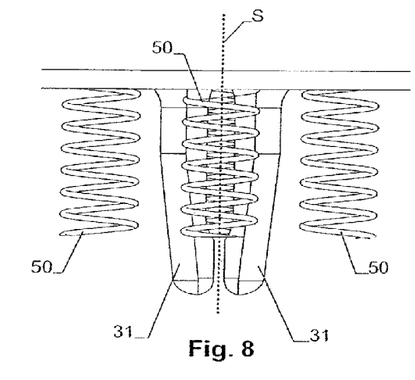
FIG. 8 shows a gripping hand with retainer springs for neighbouring samples.

In the embodiment of FIG. 8, one or more retaining springs 50 (or other elastically compressible springs) are provided on the lower side, i.e. on the sample side, of the gripping hand. The retaining springs 50 are located, seen from the axis S, radially outside of the fingers 31. If the gripping hand is lowered in order to take up one sample, the retaining springs 50 press on the neighbouring samples and hold these down, such that they cannot accidentally be lifted.

A further problem that can arise lies in the fact that, while putting down a sample, the sample sticks to the fingers 31 and can thus not be put down. This problem is solved by the embodiment of FIG. 9.

Figure 9:
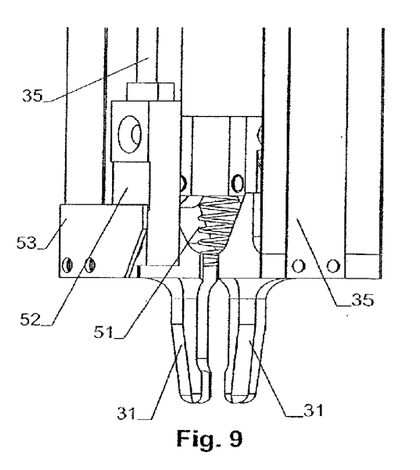
FIG. 9 shows a gripping hand with discharge spring for the sample to be taken up.

In the embodiment of FIG. 9, a discharge spring 51 is arranged between the fingers 31. Discharge spring 51 is fixedly mounted at its upper end, i.e., at its end opposite to the end of the fingers 31, while its lower end, is mounted elastically.

When the gripping hand of FIG. 9 is lowered onto a sample such that the fingers glide down on the side of the sample, the lower end of the discharge spring 51 abuts against the upper end of the sample and is compressed during the further downwards movement of the gripping hand. When, thereafter, the fingers 31 take up and lift up the sample, the discharge spring 51 stays in the compressed state until the sample is put down again and the fingers 31 are moved outwards. Then, the force of the discharge spring 51 helps to separate and eject the sample from the fingers 31.

It has to be noted that the solutions according to FIGS. 8 and 9 can also be combined. Furthermore, they are not bound to a special embodiment of the actuator of the fingers 31. They both rely on the principle of providing a spring compressible at least in a direction parallel to axis S, which is being capable of pressing axially from above against the sample to be taken up or against neighbouring samples of the sample to be taken up.

Instead of helical springs, also other spring mechanisms can be used, such as elastic foam materials.

Furthermore, in FIG. 9 a sample detector 52 is shown. It is used to detect if a sample has been gripped by the fingers 31. The sample detector 52 is fixedly attached to the carrier 33 via a support 53 and is located radially outside from one of the leaf springs 35. It comprises a proximity sensor that generates a signal as soon as the particular finger 31, and thereby the leaf spring 35, are located in their outer position in which a sample is gripped. If no sample is gripped, the sample detector 52 does not generate a signal. In this way it can reliably be determined if a sample has been successfully gripped or not.

The proximity sensor can also detect the position of one of the fingers 31 instead of the position of the leaf spring 35.

Figure 15:
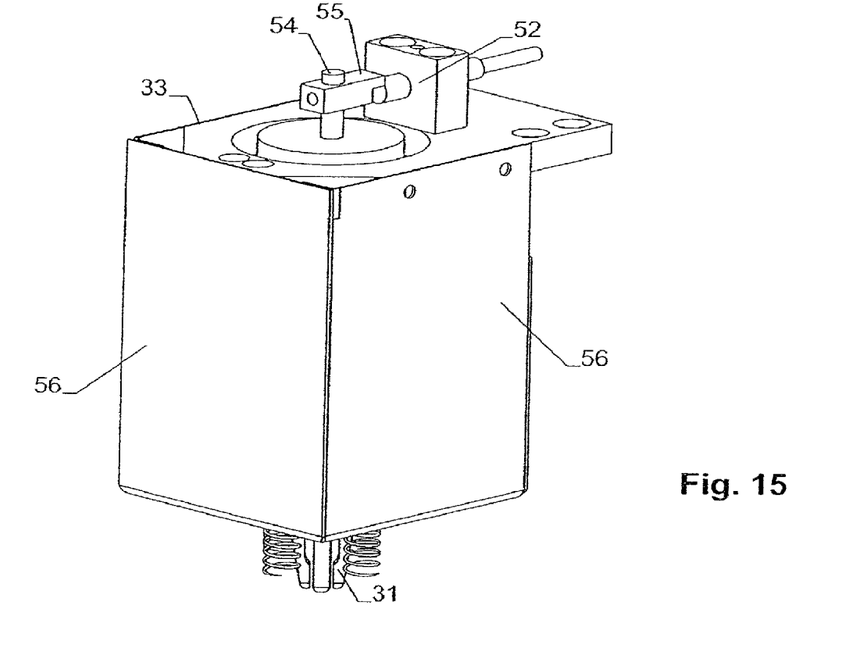
FIG. 15 shows a gripper with an alternative construction of the sample detector.

An alternative embodiment of the sample detector 52 is shown in FIG. 15. Here, the sample detector 52 is adapted to detect the axial movement of the actuation member 37. Therefore the sample detector 52 is formed as a proximity sensor detecting a head 55 which is attached at the anchor 54 of the actuation member 37. When the fingers 31 successfully grip a sample, the head 55 is located at a lower position than if the fingers 31 are empty, which is detected by the proximity sensor.

The embodiment of FIG. 15 further shows that the gripping hand can be accommodated in a housing with side walls 56.

Figure 10:
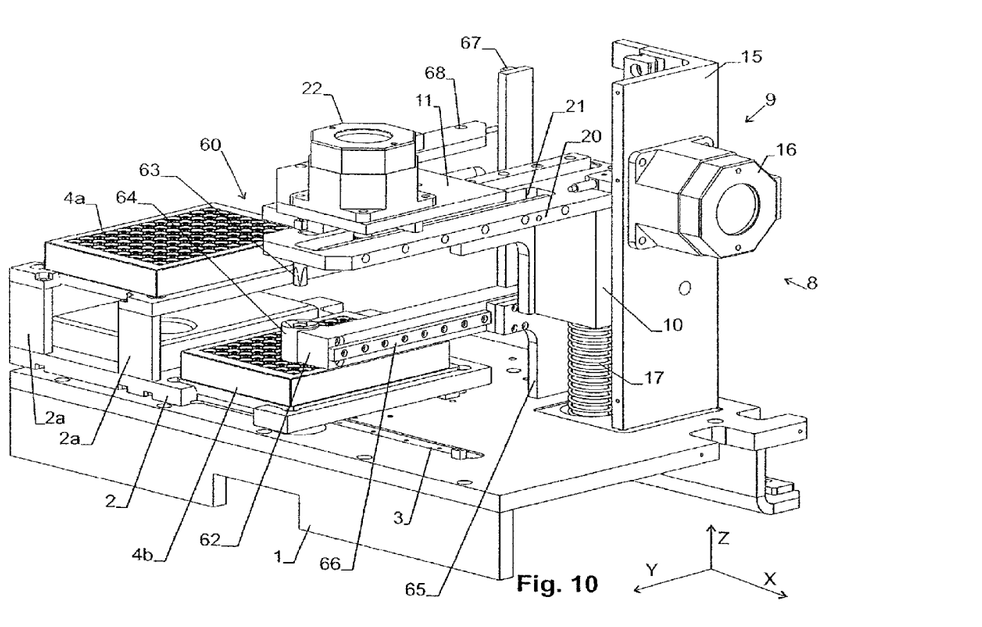
FIG. 10 shows a further embodiment of the device for handling laboratory samples.
Figures 11, 12, 13:
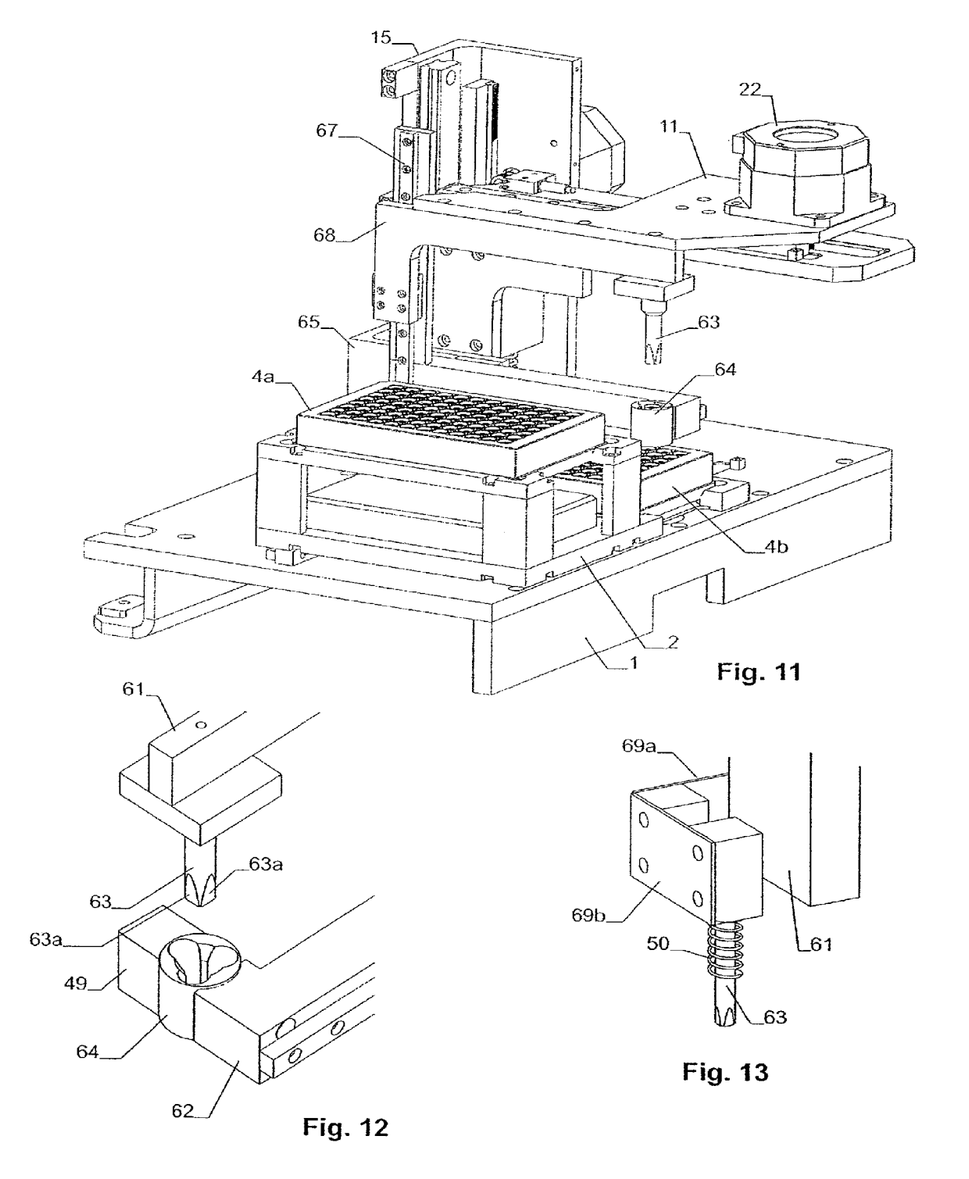
FIG. 11 shows a second view of the device of FIG. 10.
FIG. 12 shows a detail of the device of FIG. 10.
FIG. 13 shows a side view of the plunger with retainer springs.

A further embodiment of a device for handling samples is shown in FIG. 10 to 12.

Like the device according to the preceding figures, it comprises a stationary base 1, which carries a table 2. The table 2 is displaceable by an actuator in a horizontal direction X along a rail 3 and carries two sample holders 4a, 4b, which are similarly built like those according to the preceding Figures and of which each one comprises a two-dimensional arrangement of storage positions in order to take on the samples. However, a first of the sample holders, 4a, is located higher than a second of the sample holders, 4b. Therefore, on the table 2, a support 2a is provided, protruding upwards and carrying the second sample holder 4b. The sample holders 4a, 4b are preferably arranged laterally displaced to each other, such that also the lower sample holder 4b is accessible from above.

Furthermore, a manipulation device 8 is arranged on the base 1. It comprises a lift 9, which carries a wagon 10, which is displaceable in vertical direction Z. The wagon 10 carries a holder 11, which is movable in horizontal direction Y perpendicular to X and Z, and on which a an ejection device 60 is arranged.

The lift 9 is substantially built in the same way as the one according to FIG. 1 and comprises a tower 15 and a lift actuator 16, as well as a compression spring 17.

The wagon 10 comprises, on the other hand, a horizontal arm 20 with a guide 21 for the holder 11. The holder 11 comprises a horizontal actuator 22.

A first horizontal arm 61 is arranged on the holder 11 (see FIG. 12). A downwards protruding plunger 63 of the ejection device 60 is attached to arm 61. At the lower end of the plunger 63, four side surfaces 63a, which are inclined to the longitudinal axis of the plunger 63, are provided, such that the plunger tapers towards its end. The tapered form makes it possible to insert the plunger 63 in the respective sample holder 4a, 4b, even if it is not exactly aligned to the respective storage position. Because the storage positions have square cross sections, while the cross section of the samples stored therein normally are round and tubular, the square arrangement towards the tip of the plunger 63 makes it possible to push the samples securely, even in case the plunger is not exactly aligned to the sample.

In order to make a sideward displacement of the plunger 63 possible if it is inserted in a storage position that is not exactly positioned, it is advantageous to mount the plunger 63 in such a manner that it is elastically deformable or displaceable in lateral direction (i.e. in a direction transversal to its longitudinal axis). As shown in FIG. 13, the plunger 63 can e.g. be held with two parallel leaf springs 69a, 69b, wherein the planes of the leaf springs are arranged parallel to the longitudinal axis of the plunger, such that the plunger is laterally elastically displaceable, but it is fixed in its longitudinal direction.

A retaining spring 50 (or another spring member that is elastically compressible during the insertion of the plunger 63 into a storage position) can be provided as it is shown in FIG. 13. In the embodiment according to FIG. 13, the retaining spring 50 is implemented as helical spring wound around the plunger in order to save space. When the plunger 63 is lowered into a storage position of the sample holders 4a, 4b, the retaining spring 50 compresses in longitudinal direction of the plunger 63 and presses the sample holder 4a, 4b downwards, such that it is not accidentally lifted when pulling out the plunger 63.

Furthermore, an intermediate holder 65 (see FIG. 10) rests on base 1 and holds a second horizontal arm 62. The second arm 62 attached to the intermediate holder 65 by a guide 66 and slideable therein in Y-direction. A vertical guide 67 protrudes upwards from the second arm 62. The rearmost end of an interstage member 68 is arranged on the vertical guide 67 in such a manner that it is vertically slideable but horizontally fixed. The front end of the interstage member 68 is firmly connected to the holder 11.

The holder 11, and therefore also an ejection device 60, are connected via the interstage member 68 and the vertical guide 67 in such a way to the second arm 66 that each movement of the ejection device 60 in Y-direction leads to a respective movement of the second arm 62. This makes it possible to hold the ejection device 60, and particularly its plunger 63, permanently in a position precisely above intermediate storage 64 arranged on the second arm 62.

The position of the sample intermediate storage 64 in vertical direction Z is fixed and dimensioned in such a way that the sample intermediate storage 64, as well as the second arm 62, are arranged vertically between the bottom side of the upper sample holder 4a and the top side of the lower sample holder 4b.

The sample intermediate storage 64 is implemented in such a way that a sample from the top sample holder 4a can be inserted in it from above, by the plunger 63. Thereafter, the sample intermediate storage holds the sample by a frictional connection. Thereafter, the sample can be pushed out downwards into the lower sample holder 4b by a second thrust of the plunger 63.

Therefore, the device makes it possible to relocate samples from arbitrary storage positions of the upper sample holder 4a into other arbitrary storage positions of the lower sample holder 4b.

For this purpose, the table 2, as well as the holder 11, are moved in such a way that the plunger 63 comes to lie directly above the position of the sample to be pushed out of sample holder 4a. The wagon 10 is driven upwards so far that the plunger lies higher than the upper end of the sample. By way of the compulsory connection through the interstage member 68 and the vertical guide 67, the sample intermediate storage 64 and the ejection device are commonly moved in direction Y, and therefore the sample intermediate storage 64 always lies directly vertically below the sample to be pushed out.

Now the wagon 10 is lowered such that the plunger 63 pushes out the sample from the upper sample holder 4a downwards and inserts it into the sample intermediate storage 64. After that, the wagon 10 is again lifted to its previous position.

Now the table 2 and the holder 11 are moved in such a way in X direction and Y direction, respectively, that the plunger 63 and the sample intermediate storage 64 come to lie vertically above the storage position of the lower sample holder 4b into which the sample is to be dropped. Now, wagon 10 can be lowered again, such that plunger 63 pushes out the sample from the sample intermediate storage 64 and inserts it into the desired storage position of the lower sample holder 4b. Then, wagon 10 is lifted again and the sample transfer is complete.

Optionally, a mark reader 49, which is schematically shown in FIG. 12 and with which an identification mark of a sample located in the sample intermediate storage 64 can be read.

The embodiment according to FIG. 10 comprises exactly one upper sample holder. An alternative to this is the embodiment according to FIG. 14, which comprises two upper sample holders 4a, 4c. Each sample holder is arranged, by its own support 2a, on the table 2.

Figure 14:
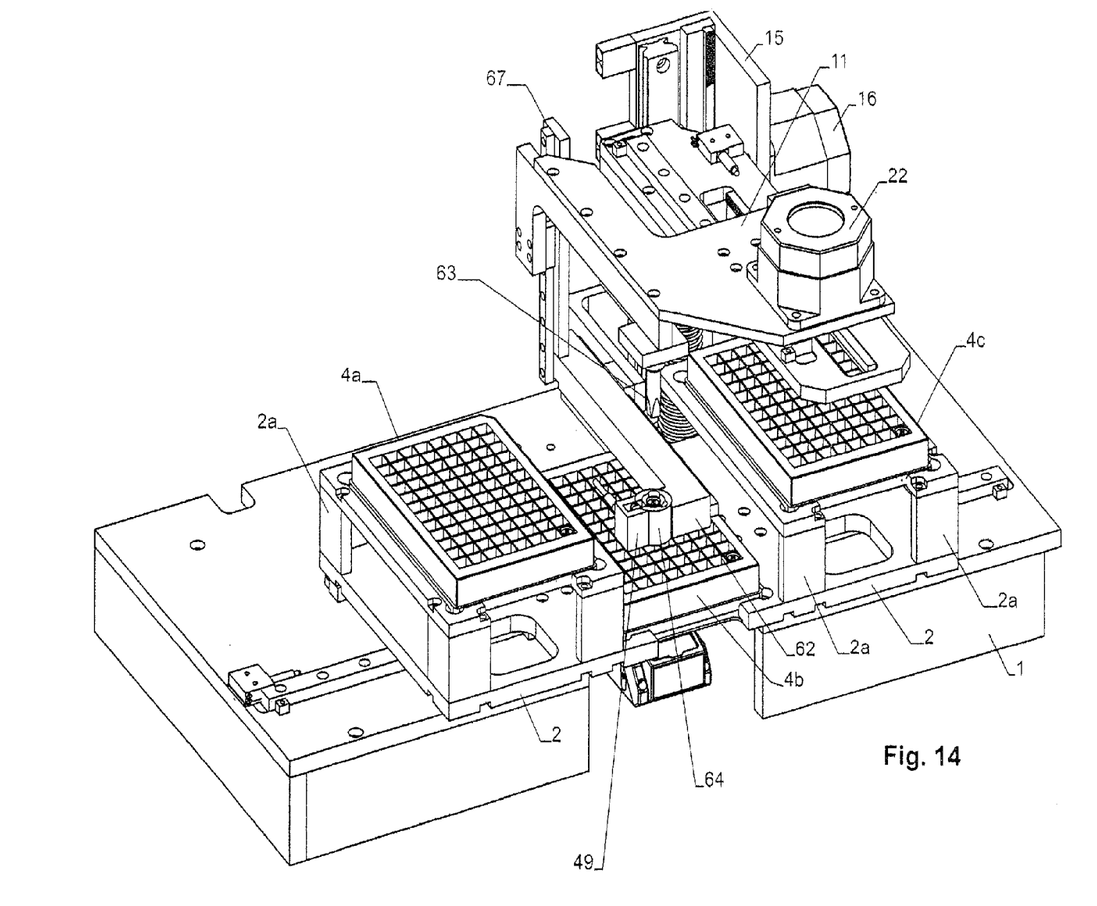
FIG. 14 shows a further embodiment of the device.

By providing space for two upper sample holders 4a, 4c, which are movable together with the table, the throughput of the sample holders can be increased for a given sample holder supply speed.

FIG. 14 further shows the mark reader 49 at the sample intermediate storage 64, which additionally or alternatively comprises a presence sensor for the detection of the presence of a sample in the sample intermediate storage 62.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims

What is claimed is:

1. A device for handling of laboratory samples, comprising:
    at least one gripper movable from above over a sample;
    the gripper including multiple fingers arranged around an axis, an elastic finger mount, and
    an actuator mechanism structured and arranged to move the fingers to selectively grip or release the sample and
    an actuation member for activation of the fingers of the gripper and being movable along the axis during actuation of the fingers of the gripper,
    wherein the multiple fingers are elastically held by the elastic finger mount in a radially displaceable manner.

2. The device of claim 1, the at least one gripper further comprising a sample detector structured and arranged to detect when a sample is gripped by the fingers.

3. The device of claim 2, further comprising a spring to which the fingers are mounted, wherein the sample detector is further structured and arranged to detect at least one of a position of at least one of one of the fingers and a position of the spring.

4. The device of claim 3, wherein the sample detector is further structured and arranged to detect the position of an actuator mechanism.

5. The device of claim 1, further comprising a mark reader structured and arranged to automatically read an identification mark positioned on the samples.

6. The device of claim 4, wherein the mark reader is stationary and wherein the device is adapted to move a sample taken be the gripper to the mark reader.

7. A device for handling of laboratory samples, comprising:
    at least one gripper movable from above over a sample;
    the gripper including multiple fingers arranged around an axis, an elastic finger mount and an actuator mechanism structured and arranged to move the fingers to selectively grip or release the sample,
    wherein the multiple fingers are elastically held by the elastic finger mount in a radially displaceable manner, and wherein the actuator mechanism comprises an actuation member which is movable along the axis, and an actuator drive for moving the actuation member along the axis during actuation of the fingers, wherein the fingers are radially movable by an axial movement of the actuation member.

8. The device of claim 4, wherein the actuation member comprises rolls, and each finger comprises a camming face oriented to be inclined to the axis, and wherein each camming face contacts at least one of the rolls.

9. The device of claim 8, wherein the actuator drive comprises an electromagnet and a piston which is movable by the electromagnet along the axis, wherein the piston is attached to the actuation member.

10. The device of claim 9, wherein the fingers have an inner position in which the sample is graspable and an outer position in which the sample is dischargeable, wherein the fingers reside in the inner position when no current flows through the electromagnet.

11. The device of claim 10, the at least one gripper further comprising at least one leaf spring holding each finger.

12. The device of claim 11, wherein each leaf spring is connected at a first end to a carrier of the gripper and at a second end opposite the first end to one of the fingers, and wherein the second end of each leaf spring is elastically movable radially to the axis.

13. The device of claim 12, wherein each leaf spring has a longitudinal direction that extends substantially parallel to the axis.

14. The device of claim 12, wherein the actuator device is fixedly connected to the carrier.

15. The device of claim 11, wherein the at least one leaf spring comprises at least two parallel, spaced-apart leaf springs attached to each finger.

16. A device for handling of laboratory samples, comprising:
    at least one gripper movable from above over a sample;
    the gripper including multiple fingers arranged around an axis, an elastic finger mount and an actuator mechanism structured and arranged to move the fingers to selectively grip or release the sample, and the at least one gripper comprising a common carrier and at least two gripping hands having fingers with different gripping diameters for gripping samples, wherein the gripping hands are arranged on the common carrier,
    the actuator mechanism comprising an actuator member to actuate the fingers, the actuator member being movable along the axis,
    wherein the multiple fingers are elastically held by the elastic finger mount in a radially displaceable manner, and wherein the at least two gripping hands are structured and arranged to grip samples having different sample diameters.

17. The device of claim 16, wherein the common carrier is pivotal at least between a first and a second working position, such that in the first working position, one of the at least two gripping hands, and, in the second working position, another of the at least two gripping hands is located to be brought in contact with the samples, and wherein the carrier is pivotable by 180° between the first and the second working position by rotating around a horizontal pivot axis.

18. A device for handling laboratory samples comprising:
at least one gripper, movable from above over a sample, having multiple fingers arranged around an axis that are laterally pushable against the sample in order to grip the sample, and an actuator mechanism for moving the fingers in order to grip and release the sample,
wherein the gripper comprises at least one spring member which is compressible parallel to the axis.

19. The device of claim 18, wherein said spring member comprises at least one spring adapted to axially push against at least one of the sample and neighboring samples of the sample to be gripped.

20. The device of claim 18, wherein the at least one gripper comprises a compressible discharge spring which is arranged between the fingers and parallel to the axis, wherein the discharge spring is structured and arranged to axially push against a gripped sample.

21. The device of claim 18, wherein the at least one gripper further comprises at least one retaining spring which is compressible parallel to the axis and which is arranged radially outside of the fingers, and wherein the at least one retaining spring is structured and arranged to axially push against neighboring samples of the sample to be gripped while the at least one gripper is gripping a sample.

* * * * *